US010420337B2

(12) United States Patent
Mayer et al.

(10) Patent No.: US 10,420,337 B2
(45) Date of Patent: Sep. 24, 2019

(54) TRANSPORTER WITH A GLUCOSE SENSOR FOR DETERMINING VIABILITY OF AN ORGAN OR TISSUE

(71) Applicant: LIFELINE SCIENTIFIC, INC., Itasca, IL (US)

(72) Inventors: Steven L. Mayer, Salem, WI (US); David C. Kravitz, Barrington Hills, IL (US); Tracey H. Mayer, Salem, WI (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 369 days.

(21) Appl. No.: 13/838,066

(22) Filed: Mar. 15, 2013

(65) Prior Publication Data

US 2014/0272923 A1 Sep. 18, 2014

(51) Int. Cl.
*A01N 1/02* (2006.01)
(52) U.S. Cl.
CPC ......... *A01N 1/0247* (2013.01); *A01N 1/0242* (2013.01); *A01N 1/02* (2013.01); *A01N 1/0273* (2013.01)
(58) Field of Classification Search
CPC ....... A01N 1/02; A01N 1/0247; A01N 1/0273
See application file for complete search history.

(56) References Cited

U.S. PATENT DOCUMENTS

| | | |
|---|---|---|
| 3,521,743 A | 7/1970 | Sposito |
| 3,712,583 A | 1/1973 | Martindale et al. |
| 3,845,974 A | 11/1974 | Pelloux-Gervais |
| 3,881,990 A | 5/1975 | Burton et al. |
| 5,013,303 A | 5/1991 | Tamari et al. |
| 5,051,352 A | 9/1991 | Martindale et al. |
| 5,149,321 A | 9/1992 | Klatz et al. |
| 5,286,718 A | 2/1994 | Elliott |
| 5,395,314 A | 3/1995 | Klatz et al. |
| 5,405,742 A | 4/1995 | Taylor |
| 5,451,524 A | 9/1995 | Coble et al. |
| 5,476,763 A | 12/1995 | Bacchi et al. |
| 5,514,536 A | 5/1996 | Taylor |
| 5,584,804 A | 12/1996 | Klatz et al. |
| 5,585,399 A | 12/1996 | Hong et al. |
| 5,599,659 A | 2/1997 | Brasile et al. |
| 5,643,712 A | 7/1997 | Brasile |
| 5,699,793 A | 12/1997 | Brasile |
| 5,702,881 A | 12/1997 | Brasile et al. |
| 5,709,654 A | 1/1998 | Klatz et al. |
| 5,752,929 A | 5/1998 | Klatz et al. |
| 5,843,024 A | 12/1998 | Brasile |
| 5,879,329 A | 3/1999 | Ginsburg |
| 5,894,266 A | 4/1999 | Wood, Jr. et al. |
| 5,928,182 A | 7/1999 | Kraus et al. |
| 6,046,046 A | 4/2000 | Hassanein |
| 6,238,908 B1 | 5/2001 | Armstrong et al. |
| 6,300,875 B1 | 10/2001 | Schafer |
| 6,492,103 B1 | 12/2002 | Taylor |
| 6,642,045 B1 | 11/2003 | Brasile |
| 6,673,594 B1 | 1/2004 | Owen et al. |
| 6,994,954 B2 | 2/2006 | Taylor |
| 7,045,279 B1 | 5/2006 | Laske et al. |
| 7,560,486 B2 | 7/2009 | Carpentier et al. |
| 8,323,954 B2 | 12/2012 | Kravitz et al. |
| 8,945,943 B2 * | 2/2015 | Lu ............................ C12Q 1/34 436/514 |
| 9,725,687 B2 * | 8/2017 | Wikswo .............. G01N 33/5088 |
| 10,078,075 B2 * | 9/2018 | Wikswo ................ B01L 3/5027 |
| 2002/0094949 A1 | 7/2002 | Paquin et al. |
| 2003/0203939 A1* | 10/2003 | Kliewer ............. A61K 31/4439 514/340 |
| 2004/0038891 A1 | 2/2004 | Bisgaier et al. |
| 2004/0224298 A1 | 11/2004 | Brassil et al. |
| 2006/0166182 A1 | 7/2006 | Weinberg et al. |
| 2010/0330547 A1 | 12/2010 | Tempelman et al. |
| 2011/0183310 A1* | 7/2011 | Kravitz et al. ................. 435/1.2 |

(Continued)

FOREIGN PATENT DOCUMENTS

| | | |
|---|---|---|
| JP | 2001-505761 A | 5/2001 |
| JP | 2005-531321 A | 10/2005 |
| JP | 2012-092111 A | 5/2012 |

OTHER PUBLICATIONS

Rushi Gandhi, James Yi, Jihyen Ha, Hang Shi, Ola Ismail, Sahra Nathoo, Joseph V. Bonventre, Xizhong Zhang, Lakshman Gunaratnam, "Accelerated receptor shedding inhibits kidney injury molecule-1 (KIM-1)-mediated efferocytosis" Am J. Physiol.—Renal Physiol., Jul. 15, 2014, 307(2), pp. F205-F221. DOI: 10.1152/ajprenal.00638. 2013.*
Xiang, Y and Lu, Y "Using personal glucose meters and functional DNA sensors to quantify a variety of analytical targets" Nat Chem. Jul. 24, 2011; 3(9): 697-703 and supplemental information (S1-S17). DOI: 10.1038/nchem.1092.*
Vallon, V; Muhlbauer, B; Osswald, H "Adenosine and Kidney Function" Physiol Rev 86: 901-940, 2006; doi:10.1152/physrev. 00031.2005.*
Vaidya et al, "Urinary Kidney Injury Molecule-1: A Sensitive Quantitative Biomarker for Early Detection of Kidney Tubular Injury" Am. J. Physiol. Renal Physiol., 2006 (pub online Sep. 20, 2005), 290, pp. F517-F529, doi:10.1152/ajprenal.00291.2005.*
Bailly, V, et al "Shedding of Kidney Injury Molecule-1, a Putative Adhesion Protein Involved in Renal Regeneration" J. Biol. Chem., Oct. 18, 2002 , 277, pp. 39739-39748, doi: 10.1074/jbc. M200562200.*

(Continued)

*Primary Examiner* — Aaron J Kosar
(74) *Attorney, Agent, or Firm* — Oliff PLC

(57) ABSTRACT

An apparatus for perfusing an organ or tissue includes a perfusion circuit for perfusing the organ or tissue with a perfusate; and a sensor operatively connected to the perfusion circuit. The sensor includes a solid support to which is attached a recognition molecule that permits detection of the target agent. The recognition molecule specifically binds to the target agent in the presence of the target agent but not significantly to other agents. The sensor also includes an enzyme that can catalyze the conversion of a substance to glucose. In the presence of the target agent the enzyme can convert the substance into glucose, which can then be detected and optionally measured by the sensor.

19 Claims, 2 Drawing Sheets

(56) References Cited

U.S. PATENT DOCUMENTS

| | | | |
|---|---|---|---|
| 2012/0315618 A1 | 12/2012 | Kravitz et al. | |
| 2012/0315621 A1* | 12/2012 | Lu | C12Q 1/34 435/5 |
| 2013/0065224 A1* | 3/2013 | Lu | C12Q 1/34 435/5 |

OTHER PUBLICATIONS

De Geus, H.R.H.; Betjes, M.G.; Bakker, J. "Biomarkers for the prediction of acute kidney injury: a narrative review on current status and future challenges" Clin Kidney J, Apr. 2, 2012, 5(2), pp. 102-108. doi: 10.1093/ckj/sfs008.*

Bonventre J.V., "Kidney injury molecule-1 (KIM-1): a urinary biomarker and much more," Nephrology Dialysis Transplantation, vol. 24, No. 11, Mar. 23, 2009, pp. 3265-3268.

Nijboer W.N. et al., "Kidney Injury Molecule-1 is an Early Non-invasive Indicator for Donor Brain Death-Induced Injury Prior to Kidney Transplantation," American Journal of Transplantation, vol. 9, No. 8, Aug. 1, 2009, pp. 1752-1759.

Sabbisetti V.S. et al., "Novel Assays for Detection of Urinary KIM-1 in Mouse Models of Kidney Injury," Toxicological Sciences, vol. 131, No. 1, Sep. 27, 2012, pp. 13-25.

Aug. 5, 2014 International Search Report issued in International Patent Application No. PCT/US2014/027998, 5 pages.

Aug. 5, 2014 Written Opinion issued in International Patent Application No. PCT/US2014/027998, 8 pages.

Sep. 28, 2012 International Search Report issued in PCT/US2012/041257, 3 pages.

Sep. 28, 2012 Written Opinion issued in PCT/US2012/041257, 8 pages.

Jochmans, Ina et al., "Graft Quality Assessment in Kidney Transplantation: Not an Exact Science Yet!" Current Opinion in Organ Transplantation, Apr. 2011, pp. 174-179, vol. 16, No. 2, Lippencott Williams & Wilkins.

Moers, Cyril et al., "The Value of Machine Perfusion Perfusate Biomarkers for Predicting Kidney Transplant Outcome," Transplantation, Nov. 2010, pp. 966-973, vol. 90, No. 9, Lippincott Williams & Wilkins.

Sep. 15, 2015 International Preliminary Report on Patentability and Written Opinion issued in PCT/US2014/027998.

Han et. al., "Kidney Injury Molecule-1 (KIM-1) A novel biomarker for human renal proximal tubule injury", vol. 62, pp. 237-244, 2002.

Oct. 19, 2016 Office Action issued in Chinese Patent Application No. 2014-80016000.9.

Mar. 14, 2018 Office Action issued in European Application No. 14726026.9.

Mar. 21, 2018 Office Action issued in Chinese Application No. 201480016000.9.

Aug. 22, 2017 Office Action issued in Chinese Application No. 201480016000.9.

\* cited by examiner

TRANSPORTER WITH A GLUCOSE SENSOR FOR DETERMINING VIABILITY OF AN ORGAN OR TISSUE

BACKGROUND

Related technical fields include organ or tissue perfusion apparatuses that are capable of sustaining and/or restoring viability of organs or tissue and preserving organs or tissues for diagnosis, treatment, storage and/or transport. For convenience, the term "organ" as used herein should be understood to mean organ and/or tissue unless otherwise specified.

It is an objective of organ perfusion apparatus to mimic conditions of the human body such that the organ remains viable before being used for research, diagnosis, treatment or transplantation. Many times the organ needs to be stored and/or transported between facilities. A goal of sustaining and restoring organs during perfusion is to reduce ischemia and reperfusion injury. The increase in storage periods in a normal or near normal functioning state also provides certain advantages, for example, organs can be transported greater distances and there is increased time for testing, treatment and evaluation of the organs.

U.S. Pat. No. 8,323,954 discloses, for example, perfusion apparatus associated with monitoring of viability of an organ by monitoring certain factors including organ resistance (pressure/flow) and/or pH, $pO_2$, $pCO_2$, LDH, T/GST, Tprotein, lactate, glucose base excess and/or ionized calcium levels in the medical fluid that has been perfused through the organ and collected.

SUMMARY

Currently hundreds of thousands of organs are donated each year for medical use. However, only a small fraction of those organs are ultimately subjectively determined to be viable and thus good candidates for diagnosis, treatment, storage and/or transport. Accordingly, it is desirable to provide an apparatus or method that determines whether organs that otherwise would be discarded could be viable and thus increase the number available for diagnosis, treatment, storage and/or transport. When an organ or tissue has been harvested, it is desirable to quickly determine whether the organ or tissue is viable. Disclosed herein is a perfusion apparatus that includes a glucose sensor that is able to detect a target agent such as a biomarker that is indicative of the viability of the organ or tissue and quantitatively measure the target agent by sensing an amount of generated glucose.

DETAILED DESCRIPTION OF EMBODIMENTS

Figure 1:
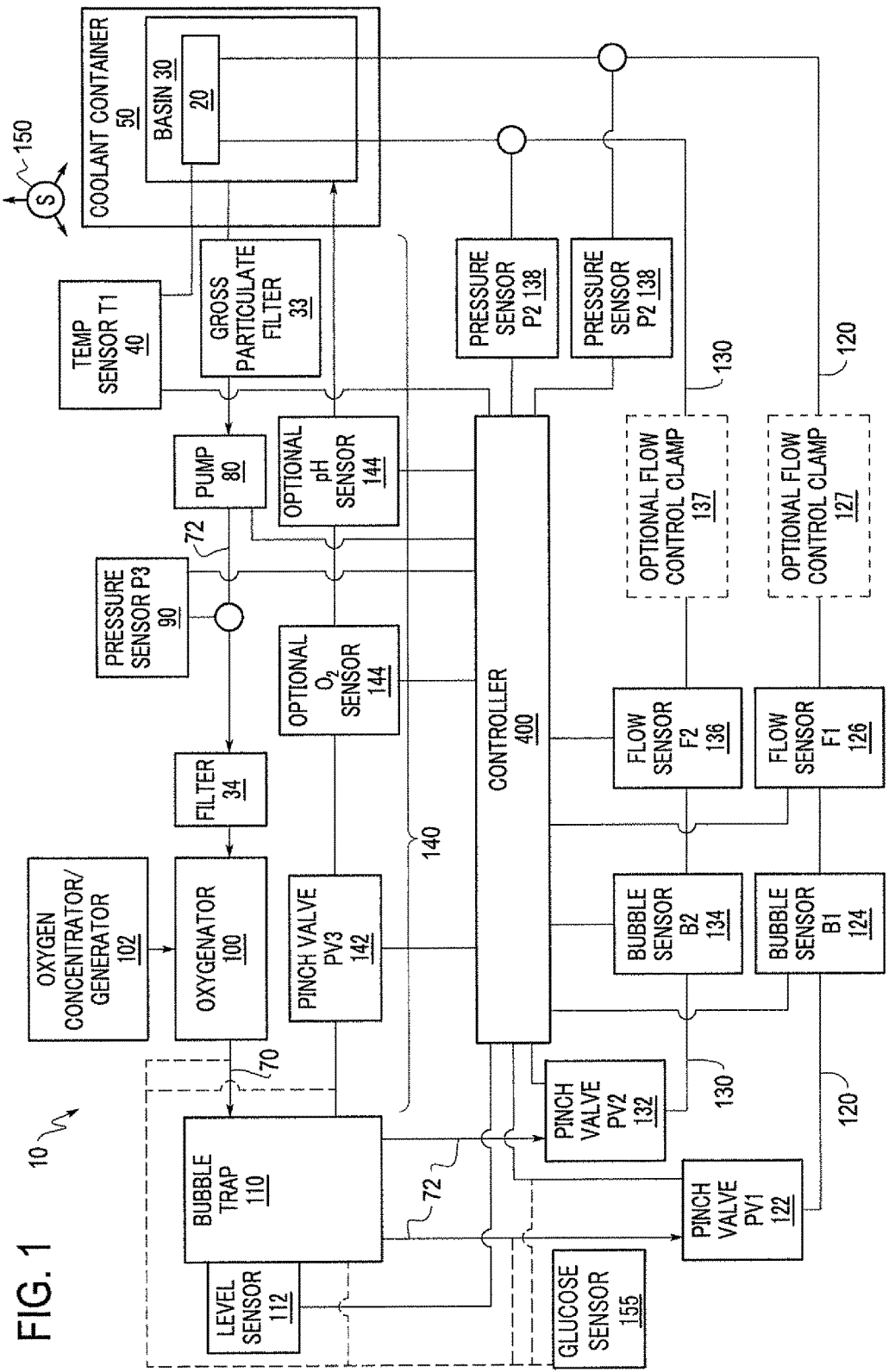
FIG. 1 is a schematic diagram of an organ perfusion apparatus according to one embodiment.

According to exemplary implementations, an apparatus is provided for sensing a biomarker or target agent in perfusate. The apparatus may include a perfusion circuit for perfusing the organ or tissue with a perfusate, and a sensor operatively connected to the perfusion circuit. The sensor may include a solid support to which is attached a recognition molecule that permits detection of a target agent, wherein the recognition molecule specifically binds to the target agent in the presence of the target agent but not significantly to other agents. The sensor may also include a substance that can be enzymatically converted to glucose and an enzyme that can catalyze the conversion of the substance to glucose, wherein the enzyme may be attached directly or indirectly to the recognition molecule, and wherein in the presence of the target agent the enzyme can convert the substance into glucose. The sensor may also include a glucose meter for detecting glucose produced from the substance. The apparatus may include a processor that outputs information regarding an amount of the glucose detected by the sensor and/or a calculated amount and other information related to the amount of the target agent to at least one of a display screen of the apparatus and an external device via a wireless communication. Preferably, the target agent is an indicator of viability of the organ or tissue. When the organ is a kidney, the target agent may, for example, be Kidney Injury Molecule-1 (KIM-1) (also known as T-cell immunoglobulin and mucin-containing molecule (TIM-1), which is a type 1 trans-membrane structural glycoprotein located in the renal proximal tubule epithelial cells. The enzyme may be attached to a KIM-1 analogue molecule that competes less strongly than KIM-1 for binding to the recognition molecule. Alternatively, the enzyme may be attached to a molecule that binds to KIM-1 that is bound to the recognition molecule. The indicator of viability could be another substance other than KIM-1 for a kidney and may be other substances for different organs.

Examples of the solid support may include a bead or a membrane. The recognition molecule may include a nucleic acid molecule, a protein, a polymer, or an antibody that specifically binds to the target agent. The enzyme, for example, may be an invertase, sucrase or sucrase-isomaltase that can convert sucrose to glucose, a maltase that can convert maltose into glucose, a trehalase that can convert trehalose into glucose, an amylase that can convert starch into glucose, or a cellulase that can convert cellulose into glucose. Preferably, the enzyme is invertase. The sensor may include a plurality of sensors with one or more or even each sensor of the plurality of sensors sensing a target agent specific to that sensor. Sensors of the plurality of sensors may each detect the same target agent or a different target agent. An example of a sensor that quantitatively detects a target agent by detecting glucose is disclosed in U.S. Patent Application Publication No. 2012/0315621, which is hereby incorporated by reference in its entirety.

Exemplary implementations include a method of determining viability of an organ or tissue. Such a method may include contacting a sensor with perfusate that is cycled through a perfusate circuit. The sensor may have a solid support to which is attached a recognition molecule that specifically binds to a viability-indicating target agent that may be in the perfusate. In embodiments, the method may include releasing an enzyme from the solid support when the viability-indicating target agent is present in the perfusate; separating the solid support from the released enzyme; contacting the released enzyme with a substance that the enzyme can convert into glucose, thereby generating glucose; detecting the glucose generated from the substance with a glucose meter; and determining viability of the organ or tissue based on the detected glucose. Other exemplary implementations include creating a target agent-recognition molecule complex by allowing the viability-indicating target agent to bind to the recognition molecule; creating a target agent-recognition molecule-enzyme recognition molecule complex by contacting the target-agent-recognition molecule complex with an enzyme that is conjugated to a second recognition molecule; contacting the enzyme with a substance that the enzyme can convert into glucose, thereby generating glucose; detecting the glucose generated from the substance with a glucose meter; and determining viability of the organ or tissue based on the detected glucose. The detection of generated glucose may indicate the presence of the viability-indicating target agent in the perfusate, and an absence of generated glucose may indicate the absence of the viability-indicating target agent in the perfusate. The method may include quantifying the target agent, a level of generated glucose detected indicating an amount of the target agent in the perfusate. The method may include comparing the amount of glucose generated with a baseline glucose level and quantitatively determining an amount of the viability-indicating target agent present in the perfusate based on a difference between the baseline glucose level and the amount of glucose detected. An example of a perfusion apparatus that may be used in connection with the present invention is disclosed in U.S. Pat. No. 8,323,954, which is hereby incorporated by reference in its entirety.

FIG. 1 is a schematic diagram of an exemplary perfusion apparatus 10 for an organ 20. The organ 20 may preferably be a liver, kidney, heart, lung or intestine, but may be any human or animal, natural or engineered, healthy, injured or diseased organ or tissue. The apparatus includes an organ support such as a basin 30 in which the organ may be placed. The basin 30 may hold a cradle on which the organ 20 is disposed when the organ 20 is in the apparatus 10. The basin 30 may include a first filter 33 that can function as a gross particulate filter. The basin 30 and/or the cradle are preferably configured to allow a perfusate bath to form around the organ 20. The basin 30 or apparatus 10 may also include a temperature sensor 40 located or focused in or near the cradle. The basin 30 or apparatus 10 may include multiple temperature sensors 40, which may provide redundancy in the event of a failure and/or may provide temperature measurement at multiple locations. Preferably, the temperature sensor(s) 40 is an infrared temperature sensor. The temperature sensor(s) 40 is preferably disposed as close as practical to the organ 20 when the organ 20 is disposed in the cradle in order to improve usefulness and accuracy of the temperature sensors 40, which preferably provide a temperature measurement of the perfusate that may be correlated to a temperature of the organ 20. Alternatively or additionally, the temperature sensor(s) 40 may be used to directly measure the temperature of the organ 20.

The basin 30 is preferably disposed within a recess of an insulating coolant container 50 that may contain cold materials such as ice, ice water, brine or the like. Coolant container 50 may be permanently or removably attached to, or an integral, monolithic part of, apparatus 10. Thus, in use in the depicted embodiment, the organ 20 is disposed within the cradle, which is disposed within the basin 30, which is disposed within the coolant container 50. The configuration of the coolant container 50, basin 30 and cradle preferably provides a configuration that provides cooling for the organ 20 without the contents of coolant container 50 contacting the organ 20 or the cradle. Although the coolant container 50 is described herein as containing ice or ice water, any suitable cooling medium can be used. Ice or ice water may be preferable due to the ease with which ice can procured, but one of ordinary skill would understand that any suitable cooling medium, which could be an active cooling medium (such as a thermo electric cooler or a refrigerant loop) or a passive cooling medium similar to ice or ice water, or a combination thereof, may be utilized. The amount of ice, or other cooling medium, that can be placed within the coolant container 50 should be determined based upon the maximum time that cooling is to be provided while the organ 20 will be in the apparatus 10.

The cradle may include components configured to securely restrain the organ 20 in place. Such components may, for example, include user selectable netting that is fastened to the cradle. The user selectable netting keeps the organ 20 in place while the organ 20 is manipulated or moved. For example, the organ may be held in place with the netting on the cradle while being manipulated (e.g., vasculature trimmed, cannulas attached, or the like) before being placed in the basin or perfusion apparatus. Similarly, the organ may be held in place when the organ 20 is moved with the cradle into the basin 30, when the basin 30 is moved into the coolant container 50 and when the apparatus 10 itself is moved during transport.

In the exemplary perfusion apparatus 10 of FIG. 1, after passing through the filter 33, the perfusate flows along a first flow path 70 that includes a suitable fluid conduit 72, such as flexible or rigid tubing, a pump 80, a pressure sensor 90, a second filter 34, an oxygenator 100 and a bubble trap 110, each of which is discussed below. In combination with one or more flow path 120 and 130 (discussed below), the first flow path 70 may form a recirculating perfusate flow path that provides perfusate to the organ 20 and then recirculates the perfusate.

The first filter 33 is preferably a relatively coarse filter (relative to the second filter 34). Such a coarse filter may be provided to prevent large particles, which may for example be byproducts of the organ or of the organ being removed from the donor, from entering and clogging fluid paths of the apparatus 10. The first filter 33 may be an integral part of the basin 30 or the first filter 33 may be disposed elsewhere in the first flow path 70 downstream of the basin 30. For example, the first filter 33 may also be a separate component from the basin 30 or disposed within the fluid conduit 72.

The first flow path 70 may also include a pump 80. The pump 80 may be any pump that is suitable in connection with perfusing of organs. Examples of suitable pumps may include hand operated pumps, centrifugal pumps and roller pumps. If a roller pump is included, the roller pump may include a single channel or flow path (where only one tube is compressed by the rollers) or the roller pump may include multiple, parallel channels or flow paths (where multiple tubes are compressed by the rollers). If multiple, parallel channels or flow paths are included, the rollers may preferably be disposed out of phase or offset so that pulses created by the rollers are out of phase, which may result in a fluid flow out of the roller pump that is relatively less pulsatile than would be the case with a single roller. Such a multiple channel roller pump may achieve a constant flow rate or a minimally pulsatile flow rate, which may be advantageous depending on the other components in the flow path and/or the type of organ being perfused.

The flow path 70 may include a pressure sensor 90. The pressure sensor 90 may preferably be disposed after the outlet of the pump 80 in order to monitor and/or be used to control the pressure produced at the outlet of the pump by way of a suitable controller 400. The pressure sensor 90 may provide continuous or periodic monitoring of pressure.

The flow path 70 may include an oxygenator 100 such as an oxygenator membrane or body to provide oxygenation to the perfusate. The oxygen may be provided by way of an oxygen reservoir, ambient air, an oxygen generator or an oxygen concentrator 102 as shown in FIG. 1, which may be separate from the apparatus 10 or integral to the apparatus 10. For example, the oxygen generator or concentrator 102 may be contained within the apparatus 10 or the oxygen generator or concentrator 102 may be an external device that can be connected to the apparatus to supply oxygen to the apparatus. Oxygen may be generated through any suitable means, some examples of which include through pressure swing adsorption using a molecular sieve (such as a zeolite), through a ceramic oxygen generator (a solid state oxygen pump) or through decomposition of water. Each type of oxygen generator or concentrator 102 discussed above may be adapted to be separate from or integral to the apparatus 10; however, some devices may be more advantageously adapted to be integral or separate. For example, an electrochemical oxygen generator may be relatively compact (on the order of a few cubic inches including a water reservoir) and therefore well suited to being integral, whereas a pressure swing adsorption device may be relatively large (due to the size of adsorbent material containers and need for a pressurized air source, such as a compressor) and therefore well suited to be separate.

The oxygen generator or concentrator 102 preferably produces oxygen in real time to provide oxygenation to the perfusate, but oxygen may also be produced and stored for short or long periods as dictated by the oxygen consumption requirements and the technology selected for producing oxygen. The oxygen generator or concentrator 102 may continuously or non-continuously produce oxygen depending on the need to oxygenate perfusate and/or the type of device used to produce the oxygen. The apparatus 10 may be configured such that there is no oxygen storage for oxygen produced from the oxygen generator or concentrator 102, except for any residual oxygen contained within plumbing or a conduit(s) from an outlet of the oxygen generator or concentrator 102 to the oxygenator 100. In other words, it may be preferable that the apparatus 10 does not include any structures specifically configured for oxygen storage. The apparatus 10 may include a device, such as a microbial filter, to ensure sterility, or otherwise prevent contamination, of the oxygen supplied to the oxygenator. Preferably such a device is located between the oxygen generator or concentrator 102 and the oxygenator 100, but may also be upstream of the oxygen generator or concentrator 102 or in both locations. Preferably, any device utilized to ensure sterility, or otherwise prevent contamination, of the oxygen supply is a disposable component. As would be appreciated by one of ordinary skill, any suitable device to ensure sterility of, or prevent contamination of, the oxygen may be provided instead of a microbial filter.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow. The bubble trap 110 may include a volume of gas, initially or through the accumulation of bubbles, such that pressure fluctuations in the perfusate are dampened or eliminated.

The bubble trap 110 may include a vent that allows purging of gas during start up or a purging process. The vent may be connected to or part of purge flow path 140 (which is discussed in detail below). The vent is preferably open during a start up process so that any air or other gas may be purged from the perfusate path 70. Once the gas is purged from the perfusate path 70, the vent may preferably be closed. The vent may be closed manually or may be closed automatically by way of controller 400.

The bubble trap 110 may include a level sensor 112. A level sensor 112 may optionally be used during the purging process to determine when the purging is complete and/or may be used to determine when the purging process needs to be repeated, which may happen after bubbles have been trapped in the bubble trap 110. Also, through the use of the level sensor 112 and the vent, the accumulator function of the bubble trap can be tuned to account for differing amplitudes and frequencies of pulsatility in the perfusate flow.

The bubble trap 110 may have any number of outlets, as needed for a given application of the perfusion apparatus. In FIG. 1, three outlets are shown connected to three different flow paths, which may be particularly suited for the perfusion of a liver. When perfusing a liver, the three paths preferably include portal flow path 120 connected to the portal vein of a liver, hepatic flow path 130 connected to the hepatic artery of a liver, and bypass flow path 140 that provides a return path to the basin 30. It is understood that the configuration illustrated in FIG. 1 could also be suited for perfusion of a kidney by eliminating, for example, hepatic flow path 130. There may also be a port in any fluid path that allows fluid access to the perfusate solution. The port may preferably be located in the bubble trap 110. This port may preferably include a liter type fitting such that a user may extract a small a sample of the perfusate for analysis. The port may also be utilized by a user to administer substances to the perfusate without opening the basin. Although FIG. 1 illustrates a single oxygenator 100 and single bubble trap 110, one of ordinary skill would appreciate that more than one oxygenator 100 and/or bubble trap 110 may be provided. For example, an oxygenator 100 and a bubble trap 110 could be provided for each of the portal flow path 120 and the hepatic flow path 130. Such a configuration may allow for different levels of oxygenation in each of the portal flow path 120 and hepatic flow path 130. A single oxygen source such as an oxygen concentrator or generator 102 may provide oxygen to both the portal flow path 120 and the hepatic flow path 130, or separate oxygen concentrators or generators 102 may be provided for each flow path. If a single oxygen concentrator or generator 102 provides oxygen to both flow paths, suitable valves such as on/off valves and/or pressure regulators may control the oxygen supplied to each flow path to be different.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs. Flow sensors 126, 136 may preferably be ultrasonic sensors disposed around tubing, although any suitable sensor may be used. Ultrasonic sensors may be advantageous because in normal usage such sensors do not come into contact with the perfusate and therefore are not in the sterile path. Such an implementation of ultrasonic sensors does not require replacement and/or cleaning after use.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Preferably, the bubble sensors 124, 134 are ultrasonic sensors disposed around tubing, although any suitable sensor may be used. Similar to pinch valves, ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles.

Flow control clamps 127, 137 may be used to fine-tune the flow rate in one or both of portal flow path 120 and hepatic flow path 130. Preferably, the organ provides self-regulation to control an amount of flow that exits the bubble trap 110 and, for a liver, is divided between the portal flow path 120 and the hepatic flow path 130. In such self regulated flow, pressure sensors 128, 138 provide overpressure monitoring. In the event that pressure delivered to the organ, for example, in either or both of the portal flow path 120 or the hepatic flow path 130, exceeds a predetermined threshold, the apparatus 10 can automatically stop and/or reduce the flow rate provided by the pump 80 to prevent damage to the organ. In addition or alternatively, the pressure sensors 128, 138 may be used to generate warning signals to the user and/or to an appropriate controller as pressures approach the predetermined threshold.

After exiting one or both of the portal flow path 120 and hepatic flow path 130, pefusate flows through the organ and returns to the basin 30 to form an organ bath.

Bypass flow path 140 may include a valve 142, and/or sensors such as oxygen sensor 144 and pH sensor 146. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 146 is only used during a purging or priming process, although it may also be used during perfusion, preferably continuously, to monitor perfusate properties in real time.

As seen in FIG. 1, a glucose sensor is provided in or connected to one or more of the flow paths. For example, the glucose sensor 155 may be provided in or connected to one or more of the first flow path 70, the portal flow path 120, the hepatic flow path 130, the purge flow path 140 and/or the bubble trap 110. Preferably, the glucose sensor 155 is provided along the purge flow path 140 adjacent to the optional oxygen sensor 144 or pH sensor 146. Although only one glucose sensor 155 is illustrated in FIG. 1, it is understood that a plurality of glucose sensors 155 may be provided. Each of the glucose sensors 155 may be configured to detect the same target agent or one or more or each may detect a different target agent. Glucose data generated by the glucose sensors 155 may be 1) analyzed by software included in testing apparatus onboard the apparatus or 2) analyzed remotely after glucose data is transmitted through wiring or wirelessly to an external device. The glucose data may be used to determine the target agent concentration and could, for example, be 1) analyzed for a specific level, 2) compared to a baseline level, or 3) analyzed together with multiple measures of target agent to generate rate of change over time data.

The glucose sensor 155 may be used to detect the presence and optionally the amount of a target, such as a target analyte/agent, through a glucose meter. The glucose sensor 155 includes a recognition molecule that is specific for the target agent and attached to a solid support, a substance that can be converted to glucose, and an enzyme that can catalyze the conversion of the substance into glucose (for example in the presence of the target agent). The enzyme can attach directly or indirectly to the recognition molecule.

The glucose meter may be any medical device for determining the approximate concentration of glucose in a sample. Glucose meters, such as a personal glucose meter (PGM), typically display the level of glucose in mg/dl or mmol/l. This disclosure is not limited to a particular brand of glucose meter, though examples include ACCU-CHEK®, ONETOUCH®, PRODIGY®, ADVOCATE®, AGAMATRIX®, ASCENSIA®, BIONIME®, CLEVERCHEK®, EASYGLUCO®, FREESTYLE®, MAXIMA®, MEDISENSE® PRESTIGE®, TRUEBALANCE®, TRUETEST® glucose meters.

Figure 2A:
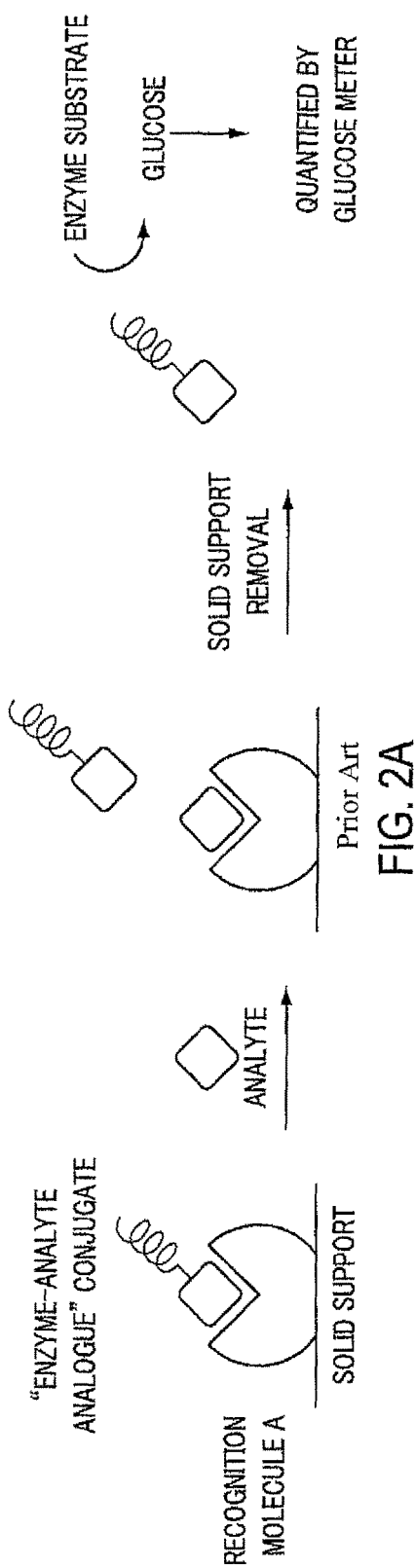
FIGS. 2A and 2B are schematic drawings showing exemplary mechanisms of target agent (analyte) detection using a glucose sensor based on the interaction between recognition molecule A, recognition molecule B and the target agent.
Figure 2B:
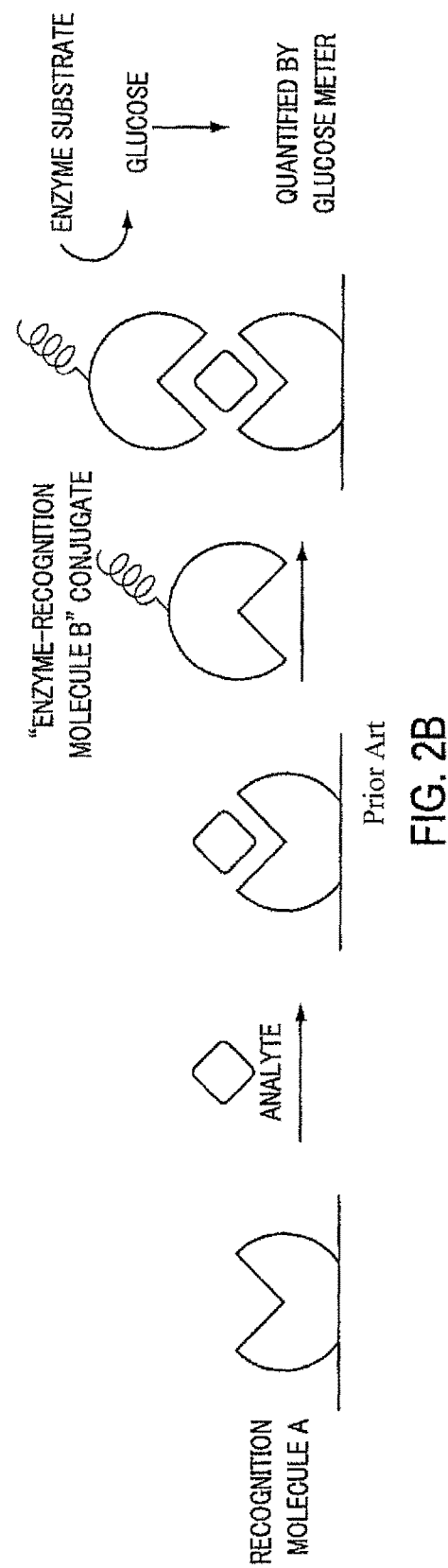

FIGS. 2A and 2B provide an overview of mechanisms that may be used in the glucose sensor 155. In FIGS. 2A and 2B, the recognition molecule A and recognition molecule B can be the same or different molecules, wherein both can bind to the analyte (referred to herein as the target agent). The enzyme that can catalyze the conversion of a substance (enzyme substrate) into glucose is conjugated with an analyte analogue (that is, an analogue of the target agent; FIG. 2A) or recognition molecule B (FIG. 2B) to form enzyme-analyte analogue conjugate (FIG. 2A) or enzyme-recognition molecule B conjugate (FIG. 2B), respectively. The enzyme substrate can be catalytically converted into glucose by the enzyme, and the glucose produced can be quantified by a glucose meter. The target agent (analyte) can be any substance that can be recognized by recognition molecule A and recognition molecule B.

FIG. 2A shows, for example, a release-based (competition) assay. Initially, enzyme-analyte analogue conjugate binds to the solid support through the interaction between enzyme-analyte analogue conjugate and recognition molecule A. When samples containing the target agent are applied to the solid support, the enzyme-analyte analogue conjugate will be released as a result of competition between enzyme-analyte analogue conjugate and target agent in binding with recognition molecule A. The concentration of enzyme-analyte analogue conjugate released can be proportional to the target agent concentration in the sample. After removal of the solid support, enzyme-analyte analogue conjugate remaining in the solution can catalyze the conversion of the enzyme substrate into glucose, which is detected by a glucose meter (sensor), and the readout is proportional to the analyte concentration.

FIG. 2B shows, for example, a binding-based (sandwich) assay. Initially, recognition molecule A is immobilized to the solid support. When a sample containing or suspected of containing the target agent (analyte) is applied to the solid support, the analyte binds to recognition molecule A. Subsequently, enzyme-recognition molecule B conjugate is added and will bind to the analyte on recognition molecule A, forming a sandwich structure. The amount of enzyme-recognition molecule B conjugate bound can be proportional to the concentration of analyte in the sample. After applying enzyme substrate (e.g., sucrose) to the solid support, the bound enzyme-recognition molecule B conjugate can convert enzyme substrate into glucose, which is detected by a glucose meter, and the readout is proportional to the analyte concentration. The enzyme is bound to the target agent, and the target agent can bind both recognition molecules A and B together. In this way, in the presence of more target agent, more enzyme will be bound to the solid support, and the bound enzyme can convert more enzyme substrate into glucose, giving a larger readout in the glucose meter.

Different types of recognition molecules, enzymes, solid supports, etc. and their different binding configurations are described, for example, in U.S. Patent Application Publication No. 2012/0315621, which is incorporated by reference herein in its entirety.

The glucose sensor 155 can be designed to detect any target agent of interest. Thus, the methods and devices provided herein can be used to detect any target agent of interest, such as the specific examples disclosed in U.S. Patent Application Publication No. 2012/0315621. Selecting an appropriate recognition molecule that permits detection of the target agent allows one to develop a sensor that can be used to detect a particular target agent. When the organ is a kidney, the target agent is preferably KIM-1; however one skilled in the art will appreciate that other target agents can be detected with the disclosed sensors and devices using the disclosed methods. Examples of different substances (such as lactate dehydrogenase, alanine aminotransferase, β-galactosidase, TNF-α, aspartate aminotransferase, IL-8, interleukins, and liver enzymes), that could be used as target agents are disclosed, for example, in U.S. Patent Application Publication No. 2012/0315618, the disclosure of which is incorporated by reference herein in its entirety. The recognition molecules could, for example, be antibodies (monoclonal or polyclonal) or aptamer based. The antibodies or aptamers have specificity to the target agent. They can be produced by known methods of antibody or aptamer production or can be purchased from OEM suppliers.

The organ perfusion apparatus 10 may also include an accelerometer 150. Preferably the accelerometer 150 is a three-axis accelerometer, although multiple single axis accelerometers may be used to the same effect. The accelerometer 150 may be used to continuously or periodically monitor and/or record the state of the apparatus 10. Monitoring may include monitoring for excessive shocks as well as attitude of the apparatus 10. By implementing such monitoring, misuse or potentially inappropriate conditions of the apparatus 10 can be detected and recorded.

The apparatus 10 may include storage compartments for items other than the organ 20. For example, the apparatus 10 may include a document compartment to store documents and/or charts related to the organ 20. Also, the apparatus 10 may include one or more sample compartment. The sample compartment may be configured, for example, to store fluid and/or tissue samples. The sample compartment may be advantageously disposed near the coolant container 50 to provide cooling, which may be similar or equivalent to the cooling provided for the organ 20.

The apparatus 10 may include one or more tamper evident closures. A tamper evident closure may be used to alert a user that the apparatus 10 has been opened at an unauthorized time and/or location and/or by an unauthorized person. Evidence of tampering may alert the user to perform additional testing, screening, or the like before using the organ 20 and/or the apparatus 10.

The organ transporter is preferably portable for carrying organs or tissues from place to place, and is sized to be carried by one or two persons and loaded into an automobile or small airplane. The perfusion apparatus 10 preferably may be an organ transporter that is designed to be portable, for example, having dimensions smaller than length 42 inches×width 18 inches×height 14 inches and a weight less than 90 lbs, which includes the weight of the complete loaded system (for example, transporter, disposable components, organ, ice and 3 liters of perfusate solution).

Methods of using the sensors and devices disclosed herein to detect a target agent are provided herein. In one example, the method includes perfusing the organ or tissue with the perfusate in the perfusion apparatus 10, contacting one or more glucose sensor 155 with perfusate under conditions sufficient to allow target agent that may be present in the perfusate to bind to the recognition molecule that is immobilized on the solid support. The disclosed glucose sensor 155 can be used in methods for detecting a target agent, for example, to determine the viability of an organ or tissue and to determine whether that organ or tissue is a good candidate for diagnosis, treatment, storage and/or transport. The method can further include quantifying the target agent, wherein a level of glucose detected indicates an amount of target agent present.

What has been described and illustrated herein are preferred embodiments of the invention along with some variations. The terms, descriptions and figures used herein are set forth by way of illustration only and are not meant as limitations. Those skilled in the art will recognize that many variations are possible within the spirit and scope of the invention.

What is claimed is:

1. An apparatus configured to perfuse an organ or tissue, the organ or tissue is an organ selected from the group consisting of a liver, a kidney, a heart, a lung, and an intestine, the apparatus comprising:
   a processor that is configured to output a determination and/or information relating to whether organs or tissues that otherwise would be discarded could be viable;
   a perfusion circuit for perfusing the organ or tissue with a perfusate, the perfusion circuit comprising a purge flow path and a recirculating perfusate flow path, wherein the recirculating perfusate flow path is configured to provide perfusate to the organ or tissue and recirculate the perfusate; and
   a plurality of sensors operatively connected to the one or more of the flow paths of the perfusion circuit, wherein the plurality of sensors includes at least:
      a first sensor in the recirculating perfusate flow path, and
      a second sensor in the purge flow path;
   where each sensor of the plurality of sensors includes:
      a solid support attached to a recognition molecule, the recognition molecule configured to specifically bind to a viability-indicating target agent in the perfusate;
      a substance that can be enzymatically converted to glucose;
      an enzyme that can catalyze conversion of the substance to glucose in the presence of the viability-indicating target agent; and
      a glucose meter configured to detect glucose produced from the substance, wherein the substance is selected from the group consisting of sucrose, maltose, trehalose, starch, and cellulose, where:
         if the substance comprises sucrose, the enzyme comprises an invertase that can convert the sucrose to glucose, a sucrase that can convert the sucrose to glucose, or a sucrase-isomaltase that can convert the sucrose to glucose,
         if the substance comprises maltose, the enzyme comprises a maltase that can convert maltose into glucose, if the substance comprises trehalose, the enzyme comprises a trehalase that can convert trehalose into glucose,
         if the substance comprises starch, the enzyme comprises an amylase that can convert starch into glucose, and
         if the substance comprises cellulose, the enzyme comprises a cellulase that can convert cellulose into glucose;

the viability-indicating target agent is an indicator of viability of the organ or tissue, the viability-indicating target agent comprising one or more members selected from the group consisting of lactate dehydrogenase, alanine aminotransferase, β-galactosidase, TNF-α, aspartate aminotransferase, IL-8, interleukins, antioxidant biomarkers, anti-apoptotic biomarkers, tropic factor biomarkers, and liver enzymes; and the processor is configured to make the determination of whether the organs or tissues that otherwise would be discarded could be viable based on an amount of glucose detected.

2. The apparatus according to claim 1, wherein the solid support comprises a bead or a membrane.

3. The apparatus according to claim 1, wherein the recognition molecule includes a nucleic acid molecule, a protein, a polymer, or an antibody that specifically binds to the viability-indicating target agent.

4. The apparatus according to claim 1, wherein each sensor of the plurality of sensors being configured to sense the presence of a viability-indicating target agent specific to that sensor.

5. The apparatus according to claim 4, wherein each sensor of the plurality of sensors is configured to detect a different viability-indicating target agent.

6. The apparatus according to claim 4, wherein each sensor of the plurality of sensors is configured to detect the same viability-indicating target agent.

7. The apparatus according to claim 1, wherein
the processor also is configured to output information regarding an amount of the glucose detected by the glucose meter of each sensor of the plurality of sensors to at least one of a display screen of the apparatus and an external device via a wireless communication.

8. The apparatus according to claim 1, wherein
the processor is configured to compare an amount of glucose detected by the glucose meter of each sensor of the plurality of sensors with a baseline glucose level and quantitatively determines an amount of the viability-indicating target agent present in the perfusate based on a difference between the baseline glucose level and the amount of glucose detected.

9. The apparatus according to claim 1, wherein the viability-indicating target agent is selected from the group consisting of interleukins, aspartate aminotransferase, and alanine aminotransferase.

10. The apparatus according to claim 1, wherein the apparatus is configured to perfuse a kidney.

11. The apparatus according to claim 1, wherein the apparatus is configured to perfuse a kidney and the viability-indicating target agent is an interleukin.

12. The apparatus according to claim 1, wherein the apparatus is configured to perfuse a liver and the viability-indicating target agent is one or more member selected from the group consisting of aspartate aminotransferase and alanine aminotransferase.

13. The apparatus according to claim 1, wherein the apparatus is configured to perfuse a liver and the viability-indicating target agent is aspartate aminotransferase.

14. The apparatus according to claim 1, wherein the apparatus is configured to perfuse a liver and the viability-indicating target agent is alanine aminotransferase.

15. The apparatus according to claim 1, wherein the apparatus is configured to perfuse a kidney and the viability-indicating target agent is one or more member selected from the group consisting of interleukins, IL-8, β-galactosidase, and TNF-α.

16. An apparatus for perfusing an organ or tissue, the apparatus being configured to perfuse a kidney or kidney tissue, the apparatus comprising:
a processor that is configured to output a determination and/or information relating to whether kidneys or kidney tissues that otherwise would be discarded could be viable;
a perfusion circuit for perfusing the kidney or kidney tissue with a perfusate, the perfusion circuit comprising a purge flow path and a recirculating perfusate flow path, wherein the recirculating perfusate flow path is configured to provide perfusate to the kidney or kidney tissue and recirculate the perfusate: and
a plurality of sensors operatively connected to the one or more of the flow paths of the perfusion circuit: wherein the plurality of sensors includes at least:
a first sensor in the recirculating perfusate flow path, and
a second sensor in the purge flow path:
where each sensor of the plurality of sensors includes:
a solid support attached to a recognition molecule, the recognition molecule configured to specifically bind to a viability-indicating target agent in the perfusate, wherein the viability-indicating target agent is Kidney Injury Molecule-1 (KIM-1);
a substance that can be enzymatically converted to glucose;
an enzyme that can catalyze conversion of the substance to glucose in the presence of the viability-indicating target agent; and
a glucose meter configured to detect glucose produced from the substance, wherein the substance is selected from the group consisting of sucrose, maltose, trehalose, starch, and cellulose, where
if the substance comprises sucrose, the enzyme comprises an invertase that can convert the sucrose to glucose, a sucrase that can convert the sucrose to glucose, or a sucrase-isomaltase that can convert the sucrose to glucose,
if the substance comprises maltose, the enzyme comprises a maltase that can convert maltose into glucose,
if the substance comprises trehalose, the enzyme comprises a trehalase that can convert trehalose into glucose,
if the substance comprises starch, the enzyme comprises an amylase that can convert starch into glucose, and
if the substance comprises cellulose, the enzyme comprises a cellulase that can convert cellulose into glucose;
the viability-indicating target agent is an indicator of viability of the kidney or kidney tissue, and
the processor is configured to make the determination of whether the organs or tissues that otherwise would be discarded could be viable based on an amount of glucose detected.

17. The apparatus according to claim 16, wherein the enzyme is attached to a KIM-1 analogue molecule that competes less strongly than KIM-1 for binding to the recognition molecule.

18. The apparatus according to claim 16, wherein the enzyme is attached to a molecule that binds to KIM-1 that is bound to the recognition molecule.

19. An apparatus for perfusing an organ or tissue, the apparatus being configured to perfuse a liver or liver tissue, the apparatus comprising:

a processor that is configured to output a determination and/or information relating to whether liver or liver tissues that otherwise would be discarded could be viable;

a perfusion circuit for perfusing the liver or liver tissue with a perfusate, the perfusion circuit comprising a purge flow path and a recirculating perfusate flow path, wherein the recirculating perfusate flow path is configured to provide perfusate to the liver or liver tissue and recirculate the perfusate: and a plurality of sensors operatively connected to the one or more of the flow paths of the perfusion circuit: wherein the plurality of sensors includes at least:
   a first sensor in the recirculating perfusate flow path, and
   a second sensor in the purge flow path:

where each sensor of the plurality of sensors includes:
   a solid support attached to a recognition molecule, the recognition molecule configured to specifically bind to a viability-indicating target agent in the perfusate, wherein the viability-indicating target agent is one or more member select from the group consisting of liver enzymes, lactate dehydrogenase and alanine aminotransferase;
   a substance that can be enzymatically converted to glucose;
   an enzyme that can catalyze conversion of the substance to glucose in the presence of the viability-indicating target agent; and
   a glucose meter configured to detect glucose produced from the substance, wherein the substance is selected from the group consisting of sucrose, maltose, trehalose, starch, and cellulose, where
     if the substance comprises sucrose, the enzyme comprises an invertase that can convert the sucrose to glucose, a sucrase that can convert the sucrose to glucose, or a sucrase-isomaltase that can convert the sucrose to glucose,
     if the substance comprises maltose, the enzyme comprises a maltase that can convert maltose into glucose,
     if the substance comprises trehalose, the enzyme comprises a trehalase that can convert trehalose into glucose,
     if the substance comprises starch, the enzyme comprises an amylase that can convert starch into glucose, and
     if the substance comprises cellulose, the enzyme comprises a cellulase that can convert cellulose into glucose:

the viability-indicating target agent is an indicator of viability of the liver or liver tissue; and the processor is configured to make the determination of whether the organs or tissues that otherwise would be discarded could be viable based on an amount of glucose detected.

\* \* \* \* \*